(12) United States Patent
Baldus et al.

(10) Patent No.: US 7,777,622 B2
(45) Date of Patent: Aug. 17, 2010

(54) MESSAGE INTEGRITY FOR SECURE COMMUNICATION OF WIRELESS MEDICAL DEVICES

(75) Inventors: Heribert Baldus, Aachen (DE); David Sanchez Sanchez, Aachen (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 423 days.

(21) Appl. No.: 11/719,099

(22) PCT Filed: Nov. 4, 2005

(86) PCT No.: PCT/IB2005/053614

§ 371 (c)(1),
(2), (4) Date: May 11, 2007

(87) PCT Pub. No.: WO2006/051461

PCT Pub. Date: May 18, 2006

(65) Prior Publication Data

US 2009/0082635 A1    Mar. 26, 2009

Related U.S. Application Data

(60) Provisional application No. 60/627,411, filed on Nov. 12, 2004.

(51) Int. Cl.
*G08B 1/08* (2006.01)
*A61B 5/00* (2006.01)

(52) U.S. Cl. ............... 340/539.12; 340/506; 340/573.1; 600/300; 600/301; 128/903; 128/904; 455/404.1

(58) Field of Classification Search ............. 340/539.12
See application file for complete search history.

(56) References Cited

U.S. PATENT DOCUMENTS 5,769,641 A    6/1998    Lampotang et al.

(Continued)

FOREIGN PATENT DOCUMENTS

JP    06084598 A    3/1994

(Continued)

*Primary Examiner*—Donnie L Crosland

(57) ABSTRACT

A system for securely synchronizing medical devices and providing message integrity with timeliness and uniqueness (10) includes a plurality of medical wireless devices ($12_1$, $12_2$, ..., $12_n$). The medical devices ($12_1$, $12_2$, ..., $12_n$) communicate wirelessly with one another. Each message (M) includes a data portion and a timestamp. Each medical device ($12_1$, $12_2$, ..., $12_n$) includes a sensor (14) which is attached to a patient to monitor a common vital sign. The medical devices ($12_1$, $12_2$, ..., $12_n$) are synchronized when the sensor (16) of each medical device detects a peak of the vital sign function. At this moment, internal clocks of each medical device ($12_1$, $12_2$, ..., $12_n$) are zeroed and each internal timer starts counting time. Thus, the medical devices are loosely synchronized at approximately the same time. Each generated message (M) is timestamped with a send time ($T_{SEND}$) generated by a time count. The generated timestamp ($T_{SEND}$) of the message (M) is validated against a receive time ($T_{RECEIVE}$) of the receiving medical device internal clock count. If the message (M) arrives out of the prespecified acceptance window, the message (M) is rejected by the receiving medical device.

17 Claims, 3 Drawing Sheets

U.S. PATENT DOCUMENTS

| | | | |
|---|---|---|---|
| 7,151,945 B2 * | 12/2006 | Myles et al. | 455/502 |
| 7,330,459 B2 * | 2/2008 | Chen et al. | 370/350 |
| 2002/0013538 A1 | 1/2002 | Teller | |
| 2002/0109621 A1 | 8/2002 | Khair et al. | |
| 2004/0076183 A1 | 4/2004 | Kobbe | |
| 2004/0176694 A1 | 9/2004 | Kim et al. | |

FOREIGN PATENT DOCUMENTS

| | | |
|---|---|---|
| JP | 2004057793 A | 2/2004 |
| WO | 9805379 A1 | 2/1998 |
| WO | 0188825 A2 | 11/2001 |
| WO | 02087681 A2 | 11/2002 |
| WO | 03009208 A1 | 1/2003 |
| WO | 03043494 A1 | 5/2003 |

* cited by examiner

US 7,777,622 B2

MESSAGE INTEGRITY FOR SECURE COMMUNICATION OF WIRELESS MEDICAL DEVICES

CROSS REFERENCE TO RELATED APPLICATIONS

This application claims the benefit of U.S. provisional application Ser. No. 60/627,411 filed Nov. 12, 2004, which is incorporated herein by reference.

The present invention relates to the medical arts. It finds particular application in conjunction with medical wireless devices and will be described with particular reference thereto. However, it is to be appreciated that the invention will also find application in conjunction with other medical devices and the like.

The wireless medical devices are increasingly deployed for continuous health care monitoring, thus forming a body area network around an individual patient. A body area sensor network is formed at the instance when the sensor nodes are attached to a patient body. In a body area network, the medical devices communicate peer-to-peer by means of ZigBee, Bluetooth, or other known short-range wireless technologies. Each medical device offers a set of medical services and can demand access to a set of medical services available on other devices.

It is essential to ensure that information being transmitted by and between the wireless medical devices is securely protected. The security of wireless communications between medical devices is typically enabled by guaranteeing message privacy and integrity. The communication data is encrypted to protect the content of transmitted messages so that intruders cannot read or modify the messages. The data integrity mechanisms enable integrity of transmitted messages so that an intruder cannot compromise communications by modifying messages and/or by first eavesdropping and then replaying messages. For instance, in a replay attack, a communication adversary can initially eavesdrop encrypted messages exchanged by authorized communicating parties, then store the eavesdropped messages and finally replay them some time later. Since the replayed messages are encrypted under the valid encryption key, communicating parties might accept them, as authentic. Acceptance of old data as authentic may have serious consequences especially in the medical domain where most of the transmitted messages contain patient vital data. Such a threat can be countered by providing message integrity with uniqueness and timeliness guarantees.

Traditionally, message integrity with uniqueness and timeliness guarantees, has been provided by cryptographically binding a timestamp to the message to be sent such as by appending a timestamp to the message and encrypting or computing a MAC of the resulting message. After decrypting the received message, an authorized receiver accepts the message if and only if the appended timestamp varies only slightly from the receiver's own current timeclock. Typically, sender and receiver have their own internal clocks "loosely synchronized" to a common time reference. In traditional infrastructure networks, such as the Internet or a LAN, computers can securely derive a common reference time from a central time server providing the common timeclock. However, in a wireless body area wireless network, wireless medical devices communicate ad hoc without connecting to any infrastructure network where a time server may reside. Moreover, because the devices are battery powered, time reference cannot be pre-configured for the whole usage life as the time reference is erased every time the medical devices run out of batteries. Additionally, their individual internal clocks tend to drift over time. Finally, since the security of message uniqueness and timeliness ultimately depends on the integrity of timeclocks, the clock synchronization procedure must be secure to prevent adversarial resetting of a clock backwards so as to restore the validity of old messages, or setting a clock forward to prepare a message for some future point in time.

The present invention provides a new and improved apparatus and method which overcomes the above-referenced problems and others.

In accordance with one aspect of the present invention, a network system is disclosed. The system comprises a plurality of medical devices for sending or receiving messages to one another, each message including a data portion and a timestamp. Each medical device includes a sensor, which is attached to the body of a patient, to at least confidentially monitor a recurring vital sign, and a timestamp generating means that generates a timestamp.

In accordance with another aspect of the present invention, a method of networking among medical devices is disclosed. Each medical device includes a sensor, which is attached to the body of a patient. At least a common recurring vital sign of the patient is securely monitored. A recurring vital sign based timestamp is generated. Messages are sent and received from one medical device to another. Each message includes a data portion and the timestamp.

One advantage of the present invention resides in automatically providing time synchronization of wireless medical devices without requiring connection to an external server to get time synchronization.

Another advantage resides in secure synchronization of wireless medical devices, whose sensors are attached to the same patient body where vital signs used for synchronization are generated.

Another advantage resides in providing time synchronization of wireless medical devices without user intervention.

Another advantage resides in automatic periodic/intermittent/occasional re-synchronization, depending on the vital sign repetition pattern.

Yet another advantage resides in reduced processing time and communication overhead required for wireless medical devices synchronization.

Still further advantages and benefits of the present invention will become apparent to those of ordinary skill in the art upon reading and understanding the following detailed description of the preferred embodiments.

The invention may take form in various components and arrangements of components, and in various steps and arrangements of steps. The drawings are only for purposes of illustrating the preferred embodiments and are not to be construed as limiting the invention.

Figure 1:
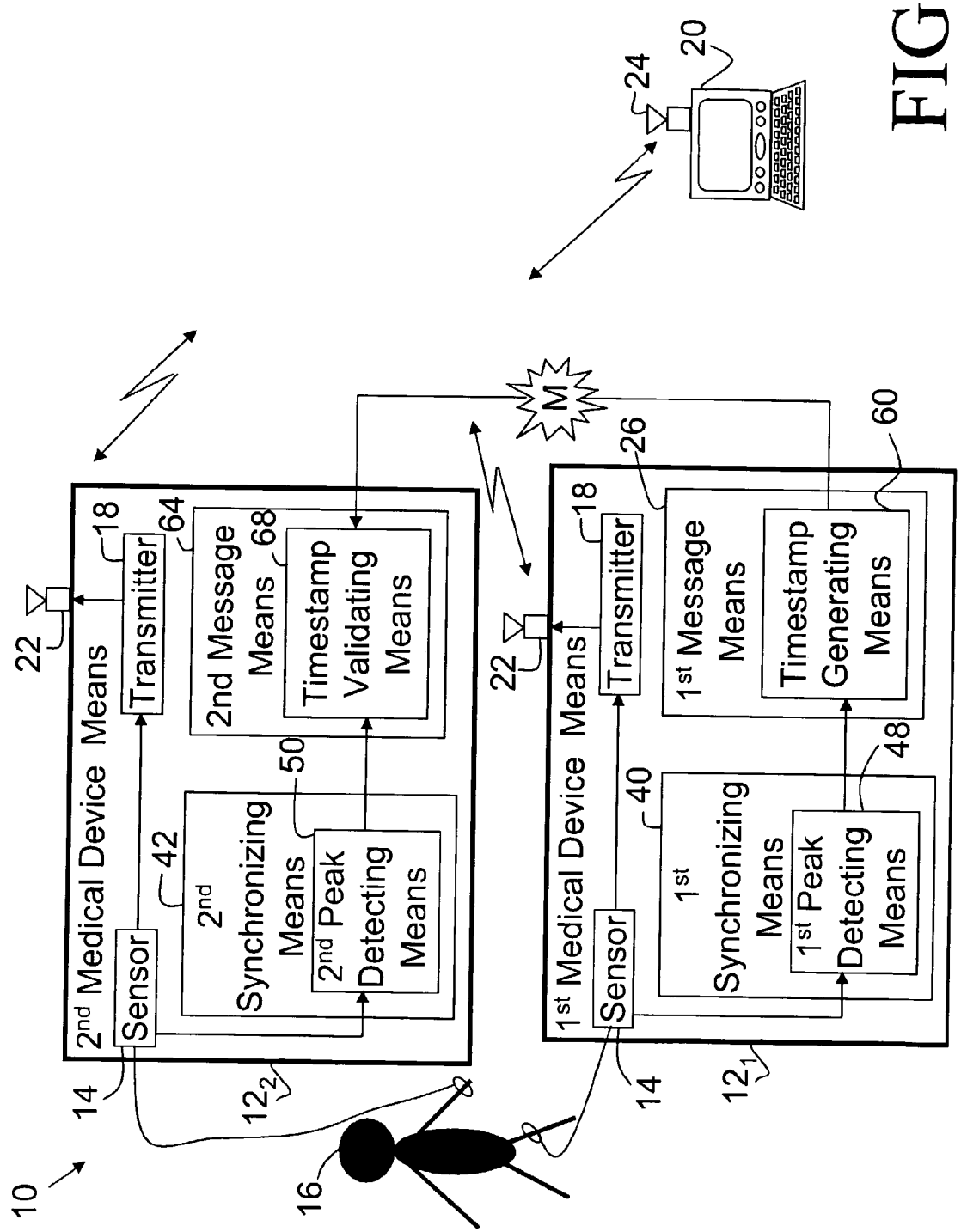
FIG. 1 is a diagrammatic illustration of a system which includes medical devices.

With reference to FIG. 1, a system for securely synchronizing medical devices and providing message integrity with timeliness and uniqueness 10 includes a plurality of medical wireless devices or means or nodes $12_1, 12_2, \ldots, 12_n$ such as ECG, blood oxygen sensor, pulse monitor, injection pump, a drip monitor, and the like. Each medical device $12_1, 12_2, \ldots, 12_n$ includes a sensor 14 which is typically disposed in close proximity to or contacting the body of a patient 16 for continuous vital sign measurements. Each medical device $12_1, 12_2, \ldots, 12_n$ further includes a transmitter 18, which wirelessly transmits the vital sign measurements to other medical devices or a (portable) bedside-monitor 20 via a transmitting/ receiving link 22, 24. The medical devices $12_1, 12_2, \ldots, 12_n$ run a communication protocol that enables a first medical device $12_1$ to distribute messages to other medical devices $12_2, 12_3, \ldots 12_n$. Preferably, prior to being attached to the patient 16, the medical devices $12_1, 12_2, \ldots, 12_n$ are initialized with shared encryption keys to ensure privacy and authenticity of communications. In one embodiment, one or more medical devices $12_1, 12_2, \ldots, 12_n$ are mobile devices that can be directly attached to the patient 16, such as wireless vital sign sensors and the like.

Figure 2:
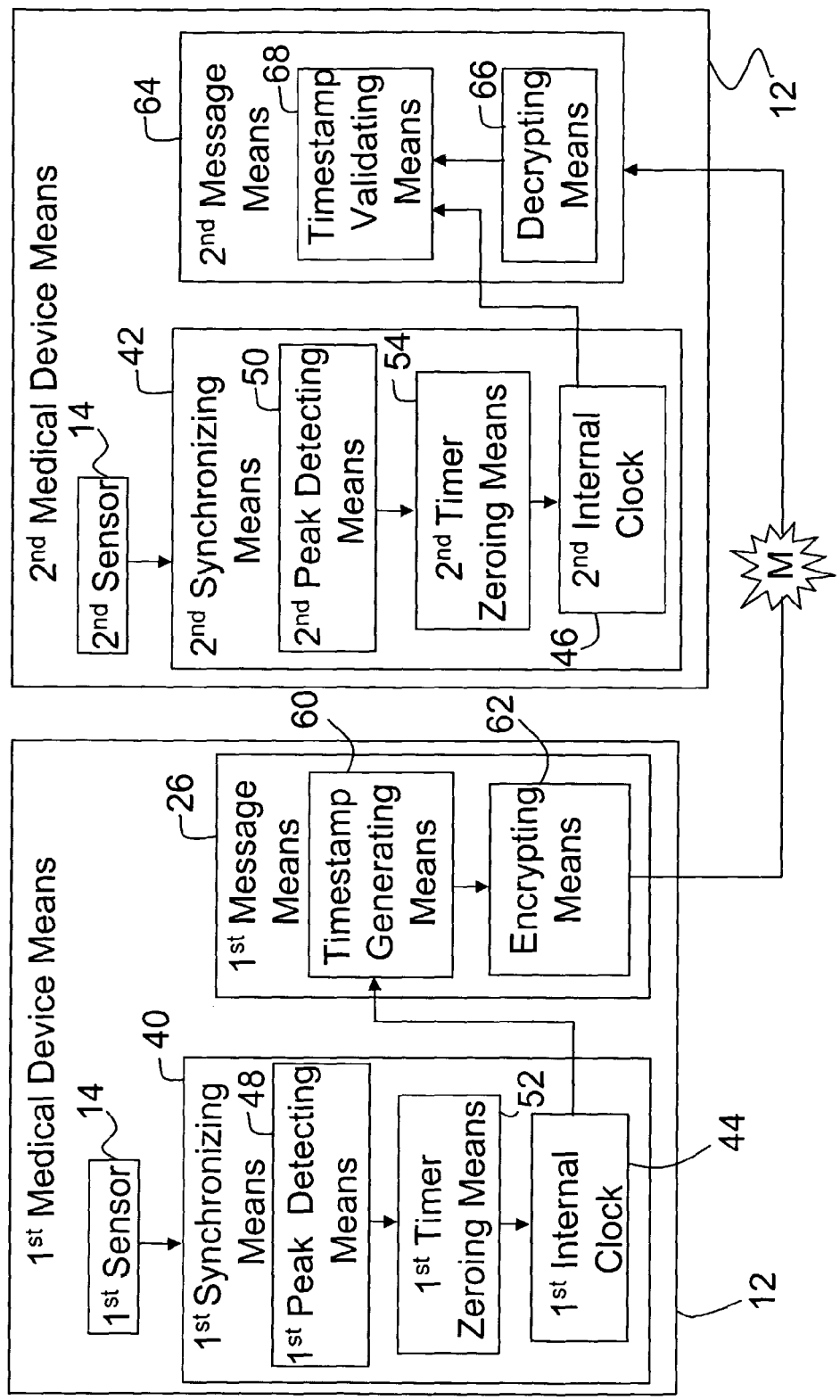
FIG. 2 is a diagrammatic illustration of a portion of a system of FIG. 1.
Figure 3:
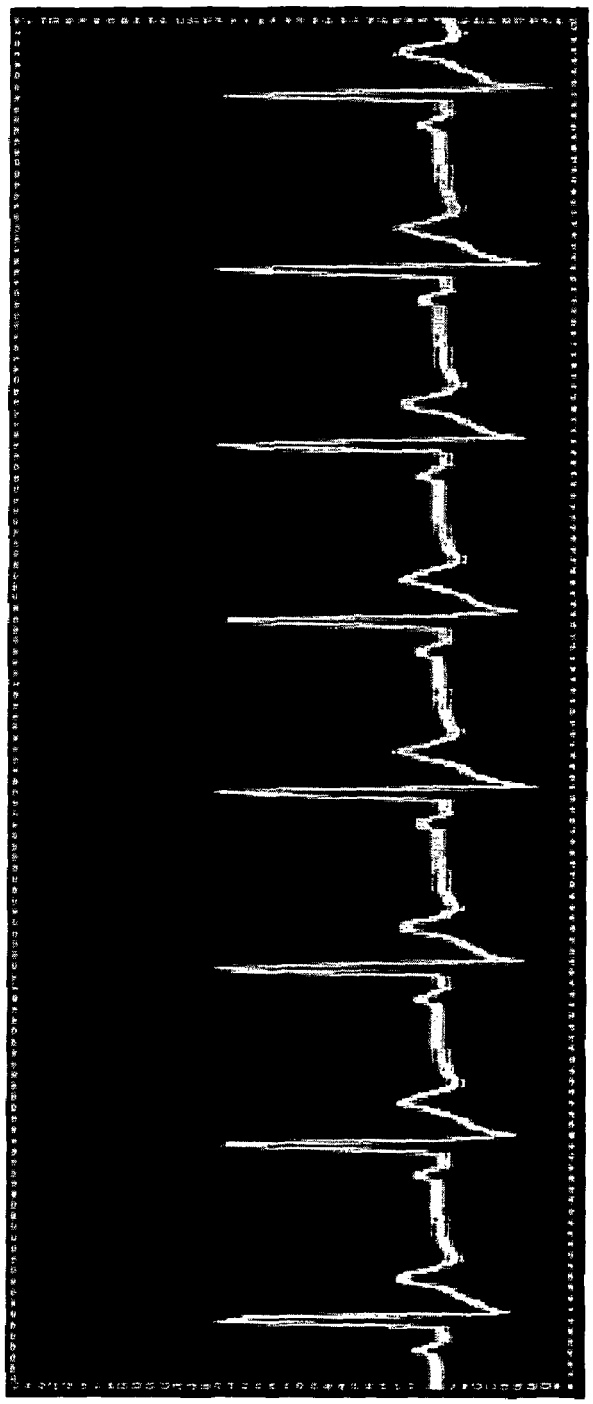
FIG. 3 is an image of an exemplary patient ECG histogram.

With continuing reference to FIG. 1 and further reference to FIGS. 2 and 3, a first medical device message means 26 generates and securely sends an encrypted and timestamped message M to a second medical device $12_2$. More specifically, each medical device $12_1, 12_2$ includes a clock synchronizing means or process 40, 42 which automatically synchronizes an associated internal clock 44, 46 of each corresponding medical device $12_1, 12_2$. A peak detecting means 48, 50 of each corresponding medical device $12_1, 12_2$ detects the vital sign peaks, e.g. a heart beat, typically one of the characteristic peaks of the ECG signal. When the peak is detected by the peak detecting means 48, 50, a timer zeroing means 52, 54 of each corresponding medical device $12_1, 12_2$ internally sets the corresponding internal clocks 44, 46 to zero, at which instance the internal clocks 44, 46 of each corresponding medical device $12_1, 12_2$ starts counting time.

In one embodiment, to improve power efficiency, instead of synchronizing continuously each time when there is a new peak of a vital sign, the medical devices $12_1, 12_2$ synchronize on demand. More specifically, instead of having the first and second peak detecting means 48, 50 to constantly monitor the peaks of the vital signs, the first message means 26 activates the first peak detecting means 48 to initiate detection of a vital sign peak. Simultaneously, the first message means 26 transmits broadcast "wake-up" to other medical devices, such as the second medical device $12_2$, of the communication system 10. As a result, the second medical device peak detecting means 50 is activated and begins detecting the vital sign peaks. When the peak is detected by the first and second peak detecting means 48, 50, the corresponding first and second timer zeroing means 52, 54 set the internal time of the first and second internal clocks 44, 46 to zero. The first and second internal clocks 44, 46 start counting time.

A first timestamp generating means 60 uses the time counted by the first internal clock 44 to generate a vital sign based timestamp $T_{SEND}$ and appends the generated timestamp $T_{SEND}$ to the message M. An encrypting means 62 encrypts the timestamped message M, and sends the message M to a second message means 64 of the second medical device $12_2$. A second medical device decrypting means 66 decrypts the message M including the appended timestamp $T_{SEND}$. The second internal clock 46 supplies a message receive internal time count value $T_{RECEIVE}$. A second medical device timestamp validating means 68 validates the timestamp $T_{SEND}$ against the message receive internal time value $T_{RECEIVE}$. If the received timestamp $T_{SEND}$ varies only slightly compared to the message receive time value $T_{RECEIVE}$, i.e. $T_{RECEIVE} - \epsilon \leq T_{SEND} \leq T_{RECEIVE} + \epsilon$, the message M is accepted. If the received timestamp $T_{SEND}$ varies significantly compared to the message receive time value $T_{RECEIVE}$, i.e. $T_{RECEIVE} - \epsilon \geq T_{SEND} \geq T_{RECEIVE} + \epsilon$, the message M is considered replayed and thus rejected. The value of E must be selected appropriately small to preclude message replay.

In one embodiment, the synchronizing process 40, 42 is terminated after a predefined timeout-period $T_{TIMEOUT}$.

In an alternate embodiment, the vital sign based timestamp includes a count of a number of repetitions of a periodic physiological function since an arbitrary reset time. For example, one of the devices sends a reset or wake up signal to all of the devices which causes them to zero a counter. Thereafter, the devices each count the number of sensed cycles, e.g. the number of R-wave peaks of the cardiac cycle, since the last reset. This count provides relative time information for the timestamp.

As another alternative, the timestamp is a combination of the number of R-wave peaks or other vital sign repetitions and the time since the last R-wave peak or other vital sign repetition.

The invention has been described with reference to the preferred embodiments. Modifications and alterations may occur to others upon a reading and understanding of the preceding detailed description. It is intended that the invention be constructed as including all such modifications and alterations insofar as they come within the scope of the appended claims or the equivalents thereof.

The invention claimed is:

1. A network system comprising:
   a plurality of medical devices for sending or receiving messages to one another, each message including a data portion and a recurring vital sign based timestamp, each medical device including:
   a sensor which is attached to a patient to at least confidentially monitor a recurring vital sign; and
   a timestamp generating means for generating the recurring vital sign based timestamp; synchronizing means for synchronizing at least first and second medical devices; wherein each synchronizing means includes:
   first and second peak detecting means for detecting a peak of the monitored recurring vital sign which is common to at least first and second medical devices.

2. A network system comprising:
   a plurality of medical devices for sending or receiving messages to one another, each message including a data portion and a recurring vital sign based timestamp, each medical device including:
   a sensor which is attached to a patient to at least confidentially monitor a recurring vital sign;
   a timestamp generating means for generating the recurring vital sign based timestamp; and
   a synchronizing means for synchronizing at least first and second communicating medical devices to evaluate a difference between a send time at which a message departs from the first medical device and a receive time at which the message arrives at the second medical device.

3. The system as set forth in claim 2, wherein each synchronizing means further includes:
   a timer zeroing means which initializes first and second internal timers of each associated medical device when a peak is detected by corresponding first and second peak detecting means, at which instance each initialized internal timer starts a new time count.

4. The system as set forth in claim 3, wherein the timestamp is indicative of the send time at about which the message leaves the first medical device and corresponds to a time gauge of the first internal timer measured from a last peak detected by the first detecting means.

5. The system as set forth in claim 4, wherein the first medical device further includes:
   an encrypting means for encrypting the message before sending it to the second medical device.

6. The system as set forth in claim 5, wherein the second medical device includes:
a timestamp validating means for comparing the affixed timestamp, which is indicative of the send time, to the receive time at which the message arrives at the second medical device, which receive time corresponds to a time gauge of the second internal timer measured from a last peak detected by the second detecting means.

7. The system as set forth in claim 2, wherein the synchronizing is performed automatically.

8. The system as set forth in claim 2, wherein the synchronizing is performed at a request of one of the medical devices.

9. A network system comprising:
a plurality of medical devices for sending or receiving messages to one another, each message including a data portion and a recurring vital sign based timestamp, each medical device including:
a sensor which is attached to a patient to at least confidentially monitor a recurring vital sign; and
a timestamp generating means for generating the recurring vital sign based timestamp, wherein the timestamp is indicative of a number of repetitions of the recurring vital sign function since a common reset time.

10. A method of networking among medical devices, which each includes a sensor, the method comprising:
attaching the sensors to a patient body;
at least monitoring a recurring vital sign of the patient;
generating a recurring vital sign based timestamp;
sending and receiving messages from one medical device to another, each message including a data portion and the timestamp;
synchronizing at least first and second communicating medical devices; and
detecting a peak of the recurring monitored common vital sign by the first and second medical devices which vital sign is common to at least first and second medical devices, and wherein the step of synchronizing includes:
automatically synchronizing the first and second medical devices to the detected peak.

11. The method as set forth in claim 10, wherein the step of synchronizing further includes:
initializing corresponding internal timers when the peak is detected by an associated first and second medical device; and
initiating a new time count in each internal timer of each associated medical device.

12. The method as set forth in claim 11, further including:
encrypting the message at the first medical device before sending the message to the second medical device;
affixing a timestamp to the message before encryption, which timestamp is indicative of the send time at about which the message leaves the first medical device and corresponds to a time gauge of the first internal timer measured from a last peak detected by the first medical device;
receiving the message at the second medical device; and
comparing the affixed timestamp to the receive time at which the message arrives at the second medical device, which receive time corresponds to a time gauge of the second internal timer measured from the last peak detected by the second medical device.

13. The method as set forth in claim 12, further including:
evaluating a difference between a send time at which a message departs from the first medical device and a receive time at which the message arrives at the second medical device.

14. The method as set forth in claim 13, further including one of:
accepting the message at the second medical device wherein the affixed timestamp substantially equals to the time gauge of the second internal timer measured from the last peak detected by the second medical device; and
rejecting the message at the second medical device wherein the affixed timestamp substantially differs from the time gauge of the second internal timer measured from a last peak detected by the second medical device.

15. A method of networking among medical devices, which each includes a sensor, the method comprising:
attaching the sensors to a patient body;
at least monitoring a recurring vital sign of the patient;
generating a recurring vital sign based timestamp;
sending and receiving messages from one medical device to another, each message including a data portion and the timestamp; and
synchronizing at least first and second communicating medical devices, wherein the step of synchronizing includes:
initiating detection of a peak of a monitored common vital sign by the first and second medical devices; and
synchronizing associated first and second internal timers when the peak is detected.

16. A method of networking among medical devices, which each includes a sensor, the method comprising:
attaching the sensors to a patient body;
at least monitoring a recurring vital sign of the patient;
generating a recurring vital sign based timestamp;
sending and receiving messages from one medical device to another, each message including a data portion and the timestamp;
synchronizing at least first and second communicating medical devices, wherein the step of synchronizing includes sending a signal to reset both the first and second medical devices and further including:
counting a number of repetitions of a common recurring vital sign; and
incorporating the count into the timestamp.

17. The method as set forth in claim 16, further including:
measuring time since a last repetition of the recurring vital sign; and incorporating the measured time into the timestamp.

* * * * *